US007148381B2

United States Patent
Arca et al.

(10) Patent No.: US 7,148,381 B2
(45) Date of Patent: Dec. 12, 2006

(54) PROCESS FOR THE ACTIVATION OF ZEOLITIC CATALYSTS CONTAINING TITANIUM AND THEIR USE IN OXIDATION REACTIONS

(75) Inventors: Vittorio Arca, Chioggia-Venezia (IT); Angelo Boscolo Boscoletto, Sottomarina-Venezia (IT); Nicola Fracasso, Dolo-Venezia (IT); Piero Furlan, Treviso (IT); Laura Meda, Galliate-Novara (IT)

(73) Assignee: Polimeri Europa S.p.A., Brindisi (IT)

( * ) Notice: Subject to any disclaimer, the term of this patent is extended or adjusted under 35 U.S.C. 154(b) by 77 days.

(21) Appl. No.: 10/481,465

(22) PCT Filed: Jun. 12, 2002

(86) PCT No.: PCT/EP02/06500

§ 371 (c)(1),
(2), (4) Date: May 3, 2004

(87) PCT Pub. No.: WO03/002254

PCT Pub. Date: Jan. 9, 2003

(65) Prior Publication Data
US 2004/0176640 A1  Sep. 9, 2004

(30) Foreign Application Priority Data
Jun. 28, 2001  (IT)  .............................. MI01A1363

(51) Int. Cl.
C07C 249/08 (2006.01)
(52) U.S. Cl. ....................................... 564/259; 564/253
(58) Field of Classification Search ..................... None
See application file for complete search history.

(56) References Cited

U.S. PATENT DOCUMENTS

| 4,410,501 A | 10/1983 | Taramasso et al. |
| 4,794,198 A * | 12/1988 | Roffia et al. ................. 564/267 |
| 5,212,302 A * | 5/1993 | Kitamura et al. ........... 540/536 |
| 5,374,747 A | 12/1994 | Saxton et al. |
| 5,403,801 A * | 4/1995 | Kitamura et al. ............. 502/86 |
| 5,591,875 A | 1/1997 | Chang et al. |
| 5,681,789 A * | 10/1997 | Saxton et al. ................. 502/85 |
| 5,695,736 A | 12/1997 | Crocco et al. |
| 5,756,778 A | 5/1998 | Roland et al. |
| 5,911,968 A | 6/1999 | Nakagawa |
| 5,912,367 A * | 6/1999 | Chang ........................ 549/529 |

FOREIGN PATENT DOCUMENTS

| DE | 100 59 520 A1 | 5/2001 |
| EP | 0 242 960 A2 | 10/1987 |
| EP | 0 712 852 | 5/1996 |
| EP | 0 712 852 A1 | 5/1996 |
| EP | 0 735 017 | 10/1996 |
| EP | 0 838 431 A1 | 4/1998 |
| EP | 0 930 308 | 7/1999 |
| EP | 1 055 663 A1 | 11/2000 |
| EP | 1 093 853  * | 4/2001 |
| GB | 2 024 790 A | 1/1980 |
| WO | WO 98/55228 | 12/1998 |
| WO | WO 99/01445 | 1/1999 |

OTHER PUBLICATIONS

Römpp Lexikon Chemie 10. Auflage, p. 1216 (1997).
A. Thangaraj, et al., Catalytic Properties of Crystalline Titanium Silicalites, Journal of Catalysis, vol. 130, pp. 1-8 (1991).

* cited by examiner

*Primary Examiner*—Brian Davis
(74) *Attorney, Agent, or Firm*—Oblon, Spivak, McClelland, Maier & Neustadt, P.C.

(57) ABSTRACT

A process is described for the activation of zeolitic catalysts containing titanium having the formula: $xTiO_2(1-x)SiO_2$ wherein x ranges from 0.0001 to 0.4, which consists in treating said materials with a solution of an ammonium salt of a carboxylic acid and subsequently subjecting them to calcination. The catalysts thus treated have higher catalytic performances with respect to those not treated, in oxidation processes of organic substrates.

19 Claims, No Drawings

PROCESS FOR THE ACTIVATION OF ZEOLITIC CATALYSTS CONTAINING TITANIUM AND THEIR USE IN OXIDATION REACTIONS

This application is a 371 of PCT/EP02/06500 filed Jun. 12, 2002.

The present invention relates to a process for the activation of zeolitic catalysts containing titanium having formula (I):

$$xTiO_2(1-x)SiO_2 \qquad (I)$$

wherein x ranges from 0.0001 to 0.4.

More specifically, the invention relates to a process for the activation of zeolitic catalysts which consists in treating said materials with a solution of an ammonium salt of a carboxylic acid and subsequently subjecting them to calcination.

The invention also relates to the materials obtained by means of the above process and to processes in which they are used as catalysts.

Zeolites, and zeolitic materials in general, are basic components for the preparation of catalysts used in numerous reactions of industrial interest.

For example, zeolites of the MFI type are known in literature as base material for the preparation of catalysts which can be used in the re-arrangement reaction of oximes to amides (EP 242,960).

Zeolites of the MFI type, in which the heteroelement supporting silicon is titanium (Titanium Silicalites TS-1), are known as catalysts used in many oxidation reactions (U.S. Pat. Nos. 4,410,501; 4,794,198).

It is also known in literature that the performances of zeolitic catalysts used in oxidation reactions in which the oxidant adopted is hydrogen peroxide added or produced by compounds capable of generating it under the reaction conditions, can be effectively improved by subjecting these catalysts to suitable activation treatment.

For example, in patent EP 230,949, the titanium silicalite pretreated with a suitable neutralizing agent of acid groups improves its selectivity in the epoxidation reactions of olefinic compounds with hydrogen peroxide.

It is known, however, that these agents, in particular those of alkaline and/or earth alkaline metals, reduce the catalytic activity more or less significantly, referring to the conversion rate of $H_2O_2$ in the time unit. In addition, they accumulate in the catalyst itself, making the thermal regeneration of the catalytic activity problematical, both in terms of maintaining the structural stability of the catalyst and also the refractory resistance in the calcination ovens where the regeneration is effected.

In patent EP 267,362, the titanium silicalite TS-1 pretreated with aqueous solutions of hydrogen peroxide and/or in the presence of at least 0.5 equivalents/liter of acids with a $pK_a \leq 5$ (preferably $H_2SO_4$, HCl, $HNO_3$, $H_3PO_4$), is particularly active in ammoximation reactions of carbonyl compounds.

In patent EP 958,861, the titanium silicalite TS-1 after activation treatment with fluoride ions or species containing fluoride, in an aqueous medium in the presence of hydrogen peroxide, improves the catalytic properties in ammoximation processes.

The activation treatment described above, however, has the great disadvantage of using chemical agents which are not easy to handle in terms of transportation, storage and use, as they create serious problems relating to corrosion of the materials and, above all, the disposal and treatment of the resulting process waste products.

It is also known that the action of these agents, with particular reference to hydro-halogen acid, results in the destructuration, by complexing, of the titanium creating a final $TiO_2$ phase which is catalytically inactive (EP 958,861).

A process has now been surprisingly found which, in addition to effectively activating zeolitic materials containing titanium in oxidation reactions with hydrogen peroxide, or compounds capable of generating it under the reaction conditions, also overcomes the drawbacks described above.

In particular, an object of the present invention relates to a process for improving the catalytic performances in oxidation reactions with zeolitic catalysts containing titanium having formula (I):

$$xTiO_2(1-x)SiO_2$$

wherein x ranges from 0.0001 to 0.4, preferably from 0.001 to 0.04 and more preferably from 0.01 to 0.03, which consists in subjecting the catalyst to treatment with an aqueous and/or aqueous-organic solution of an ammonium salt of a mono-, bi-, tri-, tetra-carboxylic acid, linear or branched, with a total number of carbon atoms ranging from 2 to 20, having general formula (II):

(II)

wherein one of the R groups is a carboxyl whereas the other R groups, the same or different, can be selected from hydrogen, hydroxyl, ether, ester, carbonyl, carboxyl, amine, amide, vinyl, hydro-halogen, nitrile, hydro-sulfide, sulfonic, phosphonic groups, etc.; or they can be selected from alkyl, cycloalkyl, alkylcycloalkyl, aromatic, alkylaromatic, aralkyl and hetero-aromatic groups, in turn substituted with one or more atoms or groups selected from hydrogen, hydroxyls, carboxyls, halogens, alkoxides, amines, esters, amides, vinyls, nitrites, hydroxyls, hydrosulfides, carbonyls, etc.; the central carbon atom of general formula (II) may or may not belong to a cycle, which can be saturated or unsaturated, hetero-aromatic with one or more hetero-atoms selected from N, O, S, etc. or non-hetero-aromatic; in the case of a cyclic substituent in formula (II), two adjacent R groups are immediately bound to the central carbon and contemporaneously belong to the cycle; this treatment is carried out for a time ranging from 0.2 to 5 hours, at concentrations of ammonium salt ranging from 0.2 to 10% by weight and is followed by the separation of the catalyst by filtration and its calcination at temperatures ranging from 300 to 650° C. for a period of time ranging from 1 to 6 hours.

In particular, examples of ammonium carboxylates useful for the purposes of the present invention are those of carboxylic acids having a $pK_a$ within the range of 4.00 to 5.15, preferably from 4.55 to 4.95, and which in solution develop a pH ranging from 6.6 to 7.4 and, more specifically from 6.9 to 7.1.

Acetic, tartaric, citric, hydroxybutyric, aminobenzoic, hexahydrobenzoic, phthalic and pyridinecarboxylic acids have proved to be particularly suitable for the purposes of the invention.

Titanium silicalites in which part of the titanium is substituted by other metals such as boron, aluminum, iron or gallium, can also be subjected to treatment. These substituted titanium silicalites and their preparation methods are described in published European patent applications 226, 257, 226,258, 266,825 and 293,032.

The treatment of the catalyst according to the invention causes an expansion in the volume of the unitary cell with respect to the initial value, as can be observed from Rietveld refinement of the XRD diffraction spectrum. Furthermore, XPS spectroscopy of the TS-1 sample treated, for example with ammonium acetate, shows that the width at mid-height of the carbon signal C(1s), centred at a Binding Energy, BE, of 285.0 eV, increases from 3.0 to 3.7 eV with respect to the non-treated sample. In particular, the C(1s) peak of the treated sample has a shoulder at a BE of 287.0 eV, which can be correlated to an ester group, not present in TS-1 as such, and which can also be observed after thermal treatment. The Si(2p) and Ti(2p) signals also broaden from 2.8 to 3.4 eV and from 3.3 to 3.9 eV, respectively, indicating a greater heterogeneity of species present after treatment with ammonium acetate.

The increase in the cell volume, on the other hand, is not observed when the treatment is effected with salts of carboxylic acid in which the ammonium ion is substituted, for example, with alkaline and/or earth alkaline cations (EP 230,949). When the treatment is effected with a sodium carboxylate, a contraction effect of the cell volume actually takes place (Example 2 and Table 1).

When, on the other hand, it is the carboxylate anion of the ammonium salt which is substituted with acid anions different from those specified above, as in the case, for example, of salts of ammonium chloride, ammonium bicarbonate, ammonium hydrate, a lesser expansion is obtained after calcination, equal to about half, of the cell volume of the catalyst (Examples 3, 4 and Table 1).

The presence of the ammonium ion, with a $pK_a$ of 9.25, in the salts of the invention makes it possible to have the necessary molarities for treating the catalyst without modifying the pH of the treatment solution which, in the case of the invention ranges from 6.6 to 7.4, preferably from 6.9 to 7.1.

The ammonium salts used in the treatment also have the particular characteristic of being able to be easily and completely removed in the subsequent thermal treatment of the catalyst, before its use, as the ammonium ion is completely degraded and removed from the zeolitic structure as well as the anions selected from the acids mentioned above. This ensures the elimination of any undesirable intervention phenomenon of the cation on the structure (modification of the crystalline class, introduction of defects, partial or complete mineralization of the structure itself) observed with other cations indicated in the known art (EP 230,949). It should be pointed out that in the known art, the use of ammonium carboxylates or other ammonium salts is exclusively connected to the use of these agents for washing zeolitic catalysts before spectroscopic analyses to remove organic residues (for example templating agents) and/or inorganic residues (for example Al and Fe) released from the materials of the synthesis plant or present as impurities in the precursors. The known art, however, does not provide any indication as to the operating procedure of the treatment or properties and/or catalytic applications of the zeolitic catalysts thus treated (R. Millini et al., *J. Catalysis*, 137, 497–503, 1992; C. Lamberti et al., *J. Catalysis*, 183, 222–231, 1999).

From a procedural point of view, the treatment according to the present invention can be effected by reflux boiling, incipient wetness impregnation or fixed bed percolation. These treatment techniques are preferred as they are easy to effect and at the same time extremely effective.

The ref lux boiling treatment is carried out by the adequate stirring of a suspension of the catalyst in an aqueous or aqueous-organic solution of the salt, and by raising the temperature to the reflux value of the suspension.

In the activation phase of the catalyst, the concentration of salt present in the treatment solution ranges from 0.2 to 10% by weight of the solution itself, preferably from 2 to 6%, more preferably from 3 to 5%.

The treatment is carried out for a time ranging from 0.5 to 5 hours, preferably from 0.5 to 3 hours and more preferably from 0.75 to 1.5 hours.

The solutions selected for the treatment can be aqueous or aqueous-organic; the organic solvent can be polar and therefore selected from alcohols, ketones, nitrites, amides, etc., or apolar such as esters, ethers, paraffins, aromatics, etc.

The catalyst is separated from the solution by filtration and, without being subjected to any washing operation, is placed directly in muffle to be calcined at temperatures ranging from 300 to 650° C. and preferably from 450 to 600° C. for a time range varying from 1 to 6 hours, preferably from 3 to 5 hours.

The calcination temperature is reached at rates ranging from 1 to 30° C./min, preferably from 5 to 20° C./min.

With the incipient wetness technique, a preliminary drying is effected at 105–110° C., under vacuum, of the titanium silicalite, followed by the actual impregnation with a solution having a volume equal to the pore volume of the catalyst and with an adequate salt content, after which it is filtered, and calcined at 550° C. for 3–5 hours.

With the fixed bed percolation technique, the solution and/or suspension of the salt is percolated on the catalyst to be treated, contained in a tubular jacketed reactor. The eluate is recovered in a tank and re-circulated with a pump to the reactor for a number of times which is sufficient to exchange the desired concentration on the catalyst.

Alternatively, it is possible to percolate the solvent alone, which elutes a fine layer of the salt, arranged on the upper part of the catalyst. The percolated product may, also in this case, be conveniently recycled, after the first passage, onto the catalyst.

The catalyst is charged and homogeneously packed into the reactor so as to eliminate preferential infiltrations of the liquid through the solid, ensuring treatment homogeneity.

The process of the present invention, although being generally valid for the activation of TS-1 in the oxidation reactions of organic substrates with hydrogen peroxide, or compounds capable of producing it under the reaction conditions, has proved to be particularly useful in ammoximation reactions of carbonyl compounds, such as, for example, cyclohexanone (U.S. Pat. No. 4,794,198; EP 496, 385).

EXAMPLE 1

10 g of TS-1 EniChem catalyst, containing 2.93% w/w of total $TiO_2$ determined by XRF (X-ray fluorescence), and 20 g of $NH_4OOCCH_3$ ($NH_4Ac$) (Carlo Erba RPE-ACS, min. tit. 98%) in 500 mL of $H_2O$, corresponding to a molar ratio $R_M(Ac/Ti)=1.5$, are charged into a 1000 mL flask equipped with a mechanical stirrer, reflux condenser, thermometer and thermostat-regulated jacket. The aqueous suspension of the catalyst is heated to reflux temperature and maintained at this value for 1 hour.

After treatment with $NH_4Ac$, the catalyst is separated from the solution by filtration, not washed with $H_2O$ (or other solvents), placed in muffle, heated at 5° C./min to 550° C. and kept at this temperature for 5 hours. XRF analysis on the catalyst thus obtained indicates a total content of $TiO_2$ equivalent to the initial value. XRD diffractometric analysis also shows an orthorhombic structure and, by means of Rietveld refinement of the spectrum, an increase in the cell volume is calculated of about 14–17 Å$^3$, from the initial value of 5371 Å$^3$ to the final value of 5385–5388 Å$^3$.

EXAMPLE 2

10 g of the same catalyst as Example 1 are treated with 500 mL of an aqueous solution in which 20 g of diammonium citrate ($NH_4Cit$) have been previously dissolved. After the treatment, the catalyst is separated by filtration, and placed directly in muffle, without intermediate washing, at 550° C. for 5 hours. XRF analysis on the catalyst thus obtained indicates a total content of $TiO_2$ equivalent to the initial value of 2.93%. XRD diffractometric analysis also shows an orthorhombic structure and, by means of Rietveld refinement of the spectrum, an increase in the cell volume is calculated of about 17 Å$^3$, from the initial value of 5371 Å$^3$ to the final value of 5388 Å$^3$.

EXAMPLE 3

Comparative 10 g of the same catalyst as Example 1 are treated with 500 mL of an aqueous solution in which 20 g of sodium acetate ($NaOOCCH_3$, NaAc) have been previously dissolved. After the treatment, the catalyst is separated by filtration, and placed directly in muffle at 550° C. for 5 hours. XRF analysis on the catalyst thus obtained indicates a total content of $TiO_2$ equivalent to the initial value of 2.93%. XRD diffractometric analysis also shows an orthorhombic structure and, by means of Rietveld refinement of the spectrum, a decrease in the cell volume is calculated of about 10 Å$^3$, from the initial value of 5371 Å$^3$ to the final value of 5361 Å$^3$.

EXAMPLE 4

Comparative

Three samples, of 10 g each, of the same catalyst as Example 1 are respectively treated with an aqueous solution 0.44 M of ammonium chloride ($NH_4Cl$), 0.50 M of ammonium bicarbonate ($NH_4HCO_3$) and 7.7 M of ammonium hydrate ($NH_4OH$). After each treatment, each catalyst is separated by filtration, and placed directly in muffle at 550° C. for 5 hours. Table 1 indicates the results of XRD diffractometric analysis which show that the orthorhombic structure has been maintained and, by means of Rietveld refinement, the unitary cell parameters. With respect to the expansion of the cell volume, 14–18 Å$^3$, determined for ammonium acetate and citrate, in all three cases, regardless of the pH value of the treatment solutions, a more limited expansion is observed, of about 8 Å$^3$, compared to the initial value of TS-1 as such of 5371 Å$^3$.

TABLE 1

Structural parameters for TS-1 not treated and treated with solutions of $NH_4Ac$, $NH_4Cit$, $NH_4Cl$, $NH_4HCO_3$, $NH_4OH$ and NaAc having varying molarities. Calcination at 550° C.

| Salt | Solution molarity (moles/L) | a (Å) | b (Å) | c (Å) | β (Å) | V (Å$^3$) | $R_p$ | $R_{wp}$ |
|---|---|---|---|---|---|---|---|---|
| — | — | 20.10125(83) | 19.92990(83) | 13.40730(64) | 90 | 5371.1(0.5) | 4.42 | 5.6 |
| $NH_4Ac$ | 0.52 | 20.12705(91) | 19.94886(76) | 13.42027(85) | 90 | 5388.4(0.6) | 3.38 | 4.39 |
| $NH_4Ac$ | 2.86 | 20.12458(93) | 19.94509(90) | 13.41879(62) | 90 | 5386.1(0.6) | 3.54 | 4.44 |
| $NH_4Ac$ | 4.42 | 20.12443(74) | 19.94229(77) | 13.41918(63) | 90 | 5385.5(0.4) | 4.52 | 5.69 |
| $NH_4Cit$ | 0.18 | 20.12959(61) | 19.94728(67) | 13.42011(52) | 90 | 5388.6(0.3) | 3.86 | 4.93 |
| $NH_4Cit$ | 1.00 | 20.13083(69) | 19.95053(75) | 13.41573(68) | 90 | 5388.0(0.6) | 3.41 | 4.34 |
| $NH_4Cit$ | 2.00 | 20.12553(86) | 19.94706(71) | 13.42027(56) | 90 | 5387.5(0.3) | 4.65 | 5.99 |
| $NH_4Cl$ | 0.44 | 20.10792(63) | 19.93869(71) | 13.41153(57) | 90 | 5377.0(0.3) | 4.08 | 5.34 |
| $NH_4HCO_3$ | 0.50 | 20.10871(88) | 19.93764(91) | 13.41304(72) | 90 | 5377.5(0.4) | 5.46 | 7.42 |
| $NH_4OH$ | 7.70 | 20.11265(75) | 19.93913(78) | 13.41483(60) | 90 | 5379.7(0.4) | 4.21 | 5.48 |
| NaAc | 0.49 | 20.09981(98) | 19.90882(79) | 13.39760(88) | 90 | 5361.2(0.5) | 3.75 | 4.87 |

X ray diffraction—WAXS: Cu $K_\alpha$ Ni filtered, E 40 KV—140 mA, range 14–101 °2Θ, step 0.02 °2Θ, t6.5 per step. $R_p$ and $R_{wp}$ reliability factors of Rietveld refinement.

EXAMPLE 5

An ammoximation reaction of cyclohexanone in a continuous manner is described, using the catalyst prepared according to the procedure of Example 1.

The reaction is carried out in equipment consisting of a 1 L steel autoclave equipped with a mechanical stirrer, automatic level control, thermostat-regulation, a device for operating at constant pressure, separate inlets for the reaction solvent, cyclohexanone and for the solution of hydrogen peroxide, and an outlet for the reaction solution equipped with a filter plug having a suitable porosity for keeping the catalyst inside the reactor.

The reaction is activated by feeding, at a constant volume in the reactor equal to 0.5 L, the reaction solvent, consisting of an azeotropic mixture of t-butyl alcohol and water (88/12 w/w) in which the necessary concentration of gaseous $NH_3$ has been previously absorbed (at least 2.5% with respect to the liquid phase), and 8.1 g of the catalyst of Example 1 (equal to 1.9% of the solution in the reactor) maintained under suspension by adequate stirring.

Once the reactor has been brought to a temperature of 85° C. and a pressure of 2.5 ata, maintained during the whole duration of the test with He, the solution of hydrogen peroxide and cyclohexanone is fed.

254.4 g/h (59% w of the solution in the reactor) of t-butyl alcohol, 34.7 g/h (8% w) of water, 23.9 g/h (5.5% w) of $NH_3$, 50.9 g/h of an aqueous solution of $H_2O_2$ with a titer of 50.01% w (equal to 5.9% w of $H_2O_2$ 100%) and 67.2 g/h (15.6% w) of cyclohexanone (One), are fed, under regime conditions, in the test described herein.

In this way, the following molar ratios ($R_M$) are obtained, in solution:

$R_M(H_2O_2/One)=1.09$; $R_M(NH_3/One)=2.04$; $R_M(NH_3/H_2O_2)=1.87$.

The test was carried out, under these conditions, without effecting any catalyst make-up, until exhaustion of the catalytic activity, obtaining the following results:

| Test duration time: | 310 hours |
| --- | --- |
| Conversion of One: | 98.6% mol (during test) |
| Selectivity to Oxime: | 99.9% mol |
| Yield of One to Oxime: | 98.5% mol |
| Yield of $H_2O_2$ to Oxime: | 90.4% mol |
| Specific catalyst consumption: | 0.35 $g_{cat}/Kg_{oximeproduced}$ |

EXAMPLE 6

Comparative

Using the same equipment and operating procedure described in Example 3, an ammoximation reaction of cyclohexanone was carried out in a continuous manner using however 8.1 g (1.9% w of the solution in the reactor) of TS-1 EniChem catalyst without any subsequent treatment (as such).

In this way, the following molar ratios ($R_M$) were registered, under regime conditions, in the reaction solution of this test:

$R_M(H_2O_2/One)=1.10$; $R_M(NH_3/One)=2.02$; $R_M(NH_3/H_2O_2)=1.84$.

The test was carried out, under these conditions, without effecting any catalyst make-up, until exhaustion of the catalytic activity, obtaining the following results:

| Test duration time: | 137 hours |
| --- | --- |
| Conversion of One: | 97.9% mol (during test) |
| Selectivity to Oxime: | 99.6% mol |
| Yield of One to Oxime: | 97.5% mol |
| Yield of $H_2O_2$ to Oxime: | 90.1% mol |
| Specific catalyst consumption: | 0.79 $g_{cat}/Kg_{oximeproduced}$ |

Table 2 below gives a direct comparison between Examples 5 and 6. It can be observed that the performances of the catalyst treated with $NH_4Ac$, Example 5, are much higher than those of the non-treated catalyst (as such), Example 6.

TABLE 2

| Performances | Unit | Example 6 Catalyst TS-1 as such | Example 5 Catalyst TS-1 $NH_4OCOCH_3$ |
| --- | --- | --- | --- |
| One conversion | mol. % | 97.9 | 98.6 |
| Selectivity to oxime | " | 99.6 | 99.9 |
| One yield to oxime | " | 97.5 | 98.5 |
| $H_2O_2$ yield to oxime | " | 90.1 | 90.4 |
| Test duration | hr | 137 | 310 |
| Catalyst specific consumption | $g_{cat}/kg_{oxime}$ | 0.79 | 0.35 |

What is claimed is:

1. A process comprising ammoximation of a carbonyl compound in the presence of hydrogen peroxide or a compound capable of producing hydrogen peroxide, and a zeolitic catalyst containing titanium having formula (I) $xTiO_2(1-x)SiO_2$ (I), wherein x ranges from 0.000 1 to 0.4, said catalyst being obtained by a process which comprises subjecting the catalyst to treatment with an aqueous and/or aqueous-organic solution of an ammonium salt of a mono-, bi-, tri-, tetra-carboxylic acid, linear or branched, with a total number of carbon atoms ranging from 2 to 20, having general formula (II)

(II)

wherein one of R1, R2, R3 and R4 is a carboxyl group, and the others of R1, R2, R3 and R4, the same or different, are selected from the group consisting of hydrogen, hydroxyl, ether, ester, carbonyl, carboxyl, amine, amide, vinyl, hydro-halogen, nitrile, hydro-sulfide, sulfonic, and phosphoric groups; or are selected from the group consisting of alkyl, cycloalkyl, alkyl-cycloalkyl, aromatic, alkylaromatic, aralkyl and hetero-aromatic groups, which groups are unsubstituted or substituted with one or more atoms or groups selected from the group consisting of hydrogen, hydroxyl, carboxyl, halogen, alkoxide, amine, ester, amide, vinyl, nitrile, hydroxyl, hydro-sulfide and carbonyl;

wherein the central carbon atom of general formula (II) may optionally form a cycle with two adjacent groups from R1, R2, R3 and R4, which cycle is saturated or unsaturated, hetero-aromatic with one or more hetero-atoms selected from the group consisting of N, O, S, or non-hetero-aromatic;

which treatment is carried out for a time ranging from 0.2 to 5 hours, at concentrations of ammonium salt ranging from 0.2 to 10% by weight and is followed by the separation of the catalyst by filtration and its calcination at temperatures ranging from 300 to 650° C. for a period of time ranging from 1 to 6 hours.

2. The process according to claim 1, wherein the catalyst is titanium silicalite TS-1 and x ranges from 0.001 to 0.04.

3. The process according to claim 2, wherein x ranges from 0.01 to 0.03.

4. The process according to claim 2, wherein in the silicalite TS-1 part of the titanium is substituted by a metal.

5. The process according to claim 4, wherein the metal comprises boron, aluminum, iron or gallium.

6. The process according to claim 1, wherein the ammonium salt is of a carboxylic acid having a $pK_a$ ranging from 4.00 to 5.15.

7. The process according to claim 6, wherein the carboxylic acid has a $pK_a$ ranging from 4.55 to 4.95.

8. The process according to claim 7, wherein the carboxylic acid is selected from the group consisting of acetic, tartaric, citric, hydroxybutyric, aminobenzoic, hexahydrobenzoic, phthalic and pyridinecarboxylic acid.

9. The process according to claim 1, wherein the pH of the aqueous and/or aqueous-organic solution ranges from 6.6 to 7.4.

10. The process according to claim 9, wherein the pH ranges from 6.9 to 7.1.

11. The process according to claim 1, wherein the concentration of salt ranges from 2 to 6%.

12. The process according to claim 10, wherein the concentration of salt ranges from 3 to 5%.

13. The process according to claim 1, wherein the treatment is carried out for a time ranging from 0.5 to 3 hours.

14. The process according to claim 13, wherein the treatment is carried out for a time ranging from 0.75 to 1.5 hours.

15. The process according to claim 1, wherein treatment is carried out with said aqueous-organic solution and the solvent of the aqueous-organic solution is a polar solvent selected from the group consisting of alcohols, ketones, nitriles, and amides, or an apolar solvent selected from the group consisting of esters, ethers, paraffins, and aromatics.

16. The process according to claim 1, wherein the catalyst is calcined at temperatures ranging from 450 to 600° C. and for a time range varying from 3 to 5 hours.

17. The process according to claim 1, wherein the calcination temperature is reached at rates ranging from 1 to 30° C./min.

18. The process according to claim 17, wherein the calcination temperature is reached at rates ranging from 5 to 20° C./min.

19. The process according to claim 1, wherein the carbonyl compound is cyclohexanone.

* * * * *